US009933342B2

(12) United States Patent
Imai et al.

(10) Patent No.: US 9,933,342 B2
(45) Date of Patent: Apr. 3, 2018

(54) METHOD FOR RENDERING BIOLOGICAL MATERIAL TRANSPARENT AND PROCESSING KIT FOR RENDERING BIOLOGICAL MATERIAL TRANSPARENT

(71) Applicant: RIKEN, Saitama (JP)

(72) Inventors: Takeshi Imai, Saitama (JP); Meng-Tsen Ke, Saitama (JP)

(73) Assignee: RIKEN, Saitama (JP)

( * ) Notice: Subject to any disclaimer, the term of this patent is extended or adjusted under 35 U.S.C. 154(b) by 212 days.

(21) Appl. No.: 14/408,647

(22) PCT Filed: Jun. 21, 2013

(86) PCT No.: PCT/JP2013/067085
§ 371 (c)(1),
(2) Date: Mar. 31, 2015

(87) PCT Pub. No.: WO2013/191274
PCT Pub. Date: Dec. 27, 2013

(65) Prior Publication Data
US 2016/0169776 A1 Jun. 16, 2016

(30) Foreign Application Priority Data
Jun. 22, 2012 (JP) .................. 2012-141488

(51) Int. Cl.
*G01N 1/30* (2006.01)
*G01N 33/48* (2006.01)
*G02B 21/34* (2006.01)
*G01N 1/36* (2006.01)

(52) U.S. Cl.
CPC .............. *G01N 1/30* (2013.01); *G02B 21/34* (2013.01); *G01N 1/36* (2013.01)

(58) Field of Classification Search
None
See application file for complete search history.

(56) References Cited

U.S. PATENT DOCUMENTS

| 6,232,092 B1 | 5/2001 | Rogers |
| 6,472,216 B1 | 10/2002 | Chiang |
| 6,703,242 B1 | 3/2004 | Senatorov |

FOREIGN PATENT DOCUMENTS

| JP | 06-080502 | 3/1994 |
| JP | 2009-285155 | 12/2009 |
| WO | 2007/089641 | 8/2007 |
| WO | 2011/111876 A1 | 9/2011 |

OTHER PUBLICATIONS

Hirshburg et al., Lasers in Surgery and Medicine, 2007, vol. 39, p. 140-144.*
European Search report of corresponding EP Application No. 13806589.1, dated Jan. 27, 2016.
Yeh, Alvin T. et al. "Molecular interactions of exogenous chemical agents with collagen—implications for tissue optical clearing" Journal of Biomedical Optics, Jan. 1, 2006, vol. 11, No. 1, p. 014003.
International Search Report of PCT/JP2013/067085 dated Sep. 10, 2013.
English translation of International preliminary report on patentability of PCT/JP2013/067085 dated Dec. 31, 2014.
Becker K. et al., "Chemical Clearing and Dehydration of GFP Expressing Mouse Brains", PLoS One, 2012, 7(3): e33916.
CelExplorerLabs, FocusClear™ Product Information, Retrieved from http://www.bio-east.com/UpFiles/20081228102521520.pdf.
Dodt H.U. et al., "Ultramicroscopy: three-dimensional visualization of neuronal networks in the whole mouse brain", Nature Methods, 2007, 4(4): 331-336.
Evageliou V. et al., "Effect of salts and sugars on the clarity of gellan gels", INt'l. J. Food Sci. Technol, vol. 46, No. 5, 2011, pp. 1001-1006.
Feng et al., "Imaging Neuronal Subsets in Transgenic Mice Expressing Multiple Spectral Variants of GFP", Neuron, 2000, 28, pp. 41-51.
Fructose Mounting Medium for Permanent Slides | MicrobeHunter Microscopy Magazine. (Dec. 31, 2008). Retrieved from http://www.microbehunter.com/fructose-mounting-medium-for-permanent-slides/.
Hama H. et al., "Scale: a chemical approach for fluorescence imaging and reconstruction of transparent mouse brain", Nature Neuroscience, 2011, 14(11): 1481-1488.
Klymkowsky and Hanken, "Whole-Mount Staining of Xenopus and Other Vertebrates", Methods in Cell Biology, 1991, 36:419-41.
Liebig C. (Dec. 10, 2010). Protocol: Optical Clearing of Samples. Retrieved from httpsworkspace.imperial.ac.ukimagingfacilityPublicoptical_clearing.pdf.
Miller C. et al. "Confocal Imaging of the Embryonic Heart: How Deep?", Microsc. Microanal., 2005, 11(3): 216-23.
Nagasaka K. et al., "Effects of Various Sugars on Properties of Agar Gel", Journal of Home Economics of Japan, 1991, vol. 42, No. 7, pp. 621-627.
Tsai P. et al., "Correclations of Neuronal and Microvascular Densities in Murine Cortex Revealed by Direct Counting and Colocalization of Nuclei and Vessels", The Journal of Neuroscience, 2009, vol. 29(46), pp. 14553-14570.
Ragan T. et al., "Serial two-photon tomography: an automated method for ex-vivo mouse brain imaging", Nat. Methods, 2012, 9(36): 255-8.

(Continued)

*Primary Examiner* — Kade Ariani
(74) *Attorney, Agent, or Firm* — Casimir Jones, SC (57) ABSTRACT

A method according to the present invention for making a biological material transparent, includes the step of: making the biological material transparent by causing a solution containing fructose to permeate into the biological material, and a kit according to the present invention for a clearing treatment for making a biological material transparent, includes a solution containing fructose.

5 Claims, 5 Drawing Sheets

(56) References Cited

OTHER PUBLICATIONS

Tang J. et al., "Gelling temperature, gel clarity and texture of gellan gels containing fructose or sucrose." Carbohydr. Polym. 2001, vol. 44, No. 3, pp. 197-209.
Tsai P. et al., "Correlations of Neuronal and Microvascular Densities in Murine Cortex Revealed by Direct Counting and Colocalization of Nuclei and Vessels," The Journal of Neuroscience, 2009, 29(46): 14553-14570.

* cited by examiner

METHOD FOR RENDERING BIOLOGICAL MATERIAL TRANSPARENT AND PROCESSING KIT FOR RENDERING BIOLOGICAL MATERIAL TRANSPARENT

CROSS-REFERENCE TO RELATED APPLICATIONS

The present application is a Section 371 U.S. national stage entry of pending International Patent Application No. PCT/JP2013/067085, International Filing Date Jun. 21, 2013, which published on Dec. 27, 2013 as Publication No. WO 2013/191274, which claims the benefit of Japanese Patent Application No. 2012-141488, filed Jun. 22, 2012, the contents of which are incorporated by reference in their entireties.

TECHNICAL FIELD

The present invention relates to, for example, a method for making a biological material transparent, and a kit for a clearing treatment for making a biological material transparent.

BACKGROUND ART

Fluorescence imaging using a fluorescent protein is an extremely effective method in the field of life science. For example, morphologies of various tissues, localization of a protein, etc. can be easily observed with use of a transgenic animal in which a fluorescent protein is expressed with use of a suitable promoter. However, a tissue normally has a considerably large thickness. Thus, it has been conventionally necessary to prepare a physical section so as to observe localization of fluorescence at a depth of the tissue.

Confocal microscopes and multiphoton excitation microscopes each for use in deep fluorescence imaging have been widespread in recent years. For example, use of multiphoton excitation microscopes allows deep imaging of approximately 300 µm to 700 µm, but more than 700 µm in depth is difficult to observe.

Several tissue clearing methods have been developed so far so that a deeper part can be observed. Known examples of the tissue clearing methods encompass a method using an aromatic organic solvent such as BABB (mixture of benzyl alcohol and benzyl benzoate 1:2 ratio), methyl salicylate, or dibenzyl ether (Non Patent Literature 1, Non Patent Literature 2, Non Patent Literature 3, and Non Patent Literature 4).

A group of Kleinfeld et al. showed in 2009 that up to 1.5 mm in depth can be observed with use of a multiphoton microscope by immersing a brain tissue in a 75% (w/v) sucrose aqueous solution (Non Patent Literature 5). A tissue clearing reagent named FocusClear™ (product name) is also commercially available (Patent Literature 1).

Further, a clearing reagent as which an aqueous solution containing urea and glycerin is employed has recently been developed (Non Patent Literature 6). This clearing reagent which is combined with a multiphoton microscope allows imaging of up to 4 mm in depth for a brain tissue.

CITATION LIST

Patent Literature

Patent Literature 1
U.S. Pat. No. 6,472,216 (Date of Patent: Oct. 29, 2002)

Non Patent Literatures

Non Patent Literature 1
Methods Cell Biol. 1991; 36:419-41.
Non Patent Literature 2
Nature Methods-4, 331-336 (2007) doi:10.1038/nmeth1036.
Non Patent Literature 3
Microsc Microanal. 2005 Jun; 11(3):216-23.
Non Patent Literature 4
PLoS ONE 7(3): e33916. (2012) doi:10.1371/journal.pone.0033916
Non Patent Literature 5
J. Neurosci, 18 Nov. 2009, 29(46): 14553-14570; doi: 10.152.
Non Patent Literature 6
Nat Neurosci. 2011 Aug. 30; 14(11):1481-8. doi: 10.1038/nn.2928.

SUMMARY OF INVENTION

Technical Problem

The method using an organic solvent (described earlier) makes it necessary to perform a dehydration treatment in advance. Since a water molecule is necessary for emission of fluorescence by a fluorescent protein, the dehydration treatment greatly reduces a fluorescence intensity of the fluorescent protein.

FocusClear™ cannot sufficiently make a tissue transparent. Further, use of FocusClear™ causes shrinkage of a sample.

According to the sucrose aqueous solution, a sample shrinks by being influenced by an osmotic pressure. Further, the sucrose aqueous solution cannot sufficiently make a tissue transparent.

Since a denaturing agent is used in the clearing reagent as which the aqueous solution containing urea and glycerin is employed, a fine structure and antigenicity of protein may be lost. Further, use of the clearing reagent causes swelling of the sample.

The present invention has been made in view of the problems, and an object of the present invention is to provide, for example, a method for making a biological material transparent without denaturing protein, and a kit for a clearing treatment for making a biological material transparent without denaturing protein.

Solution to Problem

A method according to the present invention for making a biological material transparent, includes the step of: making the biological material transparent by causing a solution containing fructose to permeate into the biological material.

A clearing reagent according to the present invention for making a biological material transparent, is a solution containing fructose.

A kit according to the present invention for a clearing treatment for making a biological material transparent, includes a solution containing fructose.

Advantageous Effects of Invention

The present invention yields an effect of allowing deep imaging by making a biological material transparent without denaturing a protein.

DESCRIPTION OF EMBODIMENTS

[Method for Making Biological Material Transparent]
(Outline)

A method according to the present invention for making a biological material transparent includes the step of: making the biological material transparent by causing a solution containing fructose (hereinafter referred to as a "clearing reagent A") to permeate into the biological material (hereinafter referred to as a "permeation step A"). The method according to the present invention for making a biological material transparent preferably further includes the step of: prior to the permeation step A, causing one or more solutions each containing fructose at a lower concentration than the clearing reagent A (hereinafter referred to as "clearing reagents B") to permeate into the biological material in an ascending order of concentration (hereinafter referred to as a "permeation step B").

Inventors of the present invention have found, for example, (i) that a biological material can be made transparent with use of a fructose solution, (ii) that a fluorescence intensity of a fluorescent protein is maintained in the biological material made transparent, and (iii) that a morphology of the biological material is well-maintained.

(Solution Containing Fructose)

The method according to the present invention for making a biological material transparent uses a solution containing fructose as an essential active component which makes a biological material transparent. Fructose may be any one of D-fructose, L-fructose, and a mixture thereof. Note that the following description may generically name the "clearing reagent A" and the "clearing reagents B" as "clearing reagents".

(Advantages of Using Fructose as Active Component)

Use of fructose as an active component has the following advantages: 1) Fructose, which is extremely low toxic, is high in safety in handling thereof. 2) Fructose, which is quite low in cost and easily available, allows a clearing treatment to be performed at an extremely low cost. 3) Fructose, which is a nondenaturing agent, is less likely to break a fine structure of a biological material and cause a loss of antigenicity due to denaturation of a protein.

In addition to the above advantages, use of fructose as an active component also has the following advantages: 4) Use of fructose, which causes no shrinkage of a biological material, is higher in transparency than use of a conventional clearing reagent. This enables an observation of various fluorescent proteins and fluorescent substances existing in ultra-deep tissues. This is also less likely to change a fine structure of a biological material. 5) Use of fructose causes no swelling of a biological material, which is less likely to be broken. This allows fructose to be applied to a fragile biological material (e.g., a newborn mouse brain). 6) Use of fructose has no influence on a strength and a cell morphology of a biological material which is returned to an isotonic solution such as PBS. Further, use of fructose allows the biological material thus returned to maintain antigenicity also in a case where the returned biological material is cut into a section and subjected to antibody staining. Imaging by a clearing treatment, which is thus highly reversible, can be combined with tissue staining. 7) Use of fructose also makes it possible to quickly make a biological material transparent. 8) Since use of fructose prevents swelling of a biological material, in a case where an objective lens of a microscope is limited in working distance, fructose allows substantially deeper image capture than a conventional clearing reagent.

(Solvent)

A "clearing reagent" used in the present invention is a solution containing a solvent in which fructose is soluble. The solvent is not particularly limited in kind, provided that fructose is soluble in the solvent. It is preferable to use water as a main solvent, and it is more preferable to use only water as the solvent. It is preferable that the "clearing reagent A" be an aqueous solution, and it is also preferable that the "clearing reagents B", which are used if necessary, be each an aqueous solution. It is more preferable that the "clearing reagent A" and the "clearing reagents B", which are used if necessary, be each an aqueous solution. Note that, in the present invention, what is meant by the expression "water is used as a main solvent" is that a volumetric percentage of water to all solvents used is larger than that of any other solvent, and preferably that water is used in an amount which accounts for more than 50% and not more than 100% of a total volume of all solvents used. Note also that, in the present invention, an "aqueous solution" refers to a solution in which water is used as a main solvent.

Main advantages of the use of water as the solvent are as follows: 1) Fructose, which is an active component of the "clearing reagent" used in the present invention, is particularly excellent in solubility in water; therefore, the use of water as the solvent makes it possible to prepare easily and at a low cost the clearing reagent. 2) Compared with a case where an organic solvent is used as a main solvent, the use of water as the solvent does not involve dehydration of a biological material to be subjected to a clearing treatment; therefore, the use of water as the solvent can prevent the problem of shrinkage of a biological material. 3) Compared with a case where an organic solvent is used as a main solvent, the use of water as the solvent significantly reduces the possibility of damaging a fluorescent protein; this makes it possible to observe, with use of a fluorescent protein, a biological material having been subjected to a clearing treatment. 4) The use of water as the solvent makes it possible to apply the clearing reagent of the present invention not only to a fixed material but also to a living material. 5) The use of water as the solvent makes a clearing treatment reversible (described later), that is, the use of water as the solvent can bring a biological material having been subjected to a clearing treatment back to a state that it had before the clearing treatment, if necessary. 6) Compared with a case where an organic solvent is used as a main solvent, the use of water as the solvent enhances safety in handling of the clearing reagent.

The fructose may be dissolved in a buffer which can maintain a pH suitable for a biological material to be subjected to a clearing treatment. Examples of a buffer to which fructose is added encompass: balanced salt solutions (e.g., PBS and HBSS) which are buffered by phosphate; and a balanced salt solution (TBS) which is buffered by tris hydrochloride. A clearing reagent which contains a buffer at a low concentration allows osmotic regulation, so that swelling of a biological sample (e.g., a newborn mouse brain) which is generally easily affected by an osmotic pressure can be more effectively prevented (e.g., 80% (w/v) fructose·0.1×PBS). Further, the "clearing reagent" which has a buffer action can further prevent a break in a fragile material and decay of fluorescence from a fluorescent protein. Note that a buffer can be an aqueous solution and that a clearing reagent in which fructose is dissolved in a buffer can be an aqueous solution.

(Permeation Step A)

The permeation step A is a step of causing the clearing reagent A to permeate into the biological material. More specifically, for example, the permeation step A is a step of causing the clearing reagent A to permeate into the biological material in a container for a clearing treatment.

A concentration at which fructose is contained in the clearing reagent A is not particularly limited. Fructose is contained preferably at a concentration falling within a range of 20% or more and not more than 150% of a saturated concentration, more preferably at a concentration falling within a range of 50% or more and not more than 120% of the saturated concentration, still more preferably at a concentration falling within a range of 80% or more of the saturated concentration and not more than the saturated concentration (100%), and particularly preferably at the saturated concentration (100%). Note that a saturated concentration represented by a unit "% (w/v)" depends on a temperature, and the "saturated concentration" herein means a saturated concentration at a temperature at which the permeation step A is performed. This allows a person skilled in the art to prepare, in accordance with the temperature at which the permeation step A is performed, the clearing reagent A at the saturated concentration or the clearing reagent A at a concentration that is equivalent to a desired percentage of the saturated concentration. Note that the unit "% (w/v)" is a percentage of a weight (w (gram)) of "fructose" used to a volume (v (milliliter)) of the "clearing reagent".

Fructose may be contained in the clearing reagent A preferably at a concentration of 50% (w/v) or more and not more than 200% (w/v), more preferably at a concentration of 80% (w/v) or more and not more than 150% (w/v), and still more preferably at a concentration of 100% (w/v) or more and not more than 140% (w/v). At 25° C., a concentration of 100% (w/v) or more and not more than 120% (w/v) is a particularly preferable example, and above all, the concentration is particularly preferably approximately 110% (w/v). At 37° C., a concentration of 120% (w/v) or more and not more than 140% (w/v) is a particularly preferable example, and above all, the concentration is particularly preferably approximately 130% (w/v).

The temperature at which the permeation step A is performed is not particularly limited. From the viewpoint of a saturated concentration and prevention of a side reaction of fructose, the permeation step A is preferably performed at a temperature falling within a range of 0° C. or more and not more than 40° C. A time for which the permeation step A is performed is not particularly limited. The permeation step A is performed for a time falling within a range preferably of one hour or more and not more than 14 days, and more preferably of 12 hours or more and not more than three days. A pressure at which the permeation step A is performed is not particularly limited.

(Permeation Step B)

The permeation step B, which is performed if necessary, is a step of prior to the permeation step A, causing one or more clearing reagents B each containing fructose at a lower concentration than the clearing reagent A to permeate into the biological material in an ascending order of concentration. More specifically, the permeation step B is a step of causing one or more clearing reagents B to permeate into the biological material in an ascending order of concentration in the container for the clearing treatment.

A concentration at which fructose is contained in each of the clearing reagents is not particularly limited, provided that the concentration is lower than that of fructose contained in the clearing reagent A. By performing the permeation step B prior to the permeation step A, it is possible to prevent a rapid increase in concentration of fructose and thus further prevent damage to the biological material. It is preferable to use two or more clearing reagents B which differ from each other in concentration, it is more preferable to use three or more clearing reagents B which differ from each other in concentration, and it is still more preferable to use four or more clearing reagents B which differ from each other in concentration. This is because a more minute and gradual increase in concentration can further prevent damage to the biological material.

It is preferable to substantially uniformly increase concentrations of fructose contained in the clearing reagents B. For example, in a case where fructose is contained in the clearing reagent A at a concentration of 110% (w/v), it is possible to use, as the clearing reagents B, five solutions in which fructose is contained at respective concentrations of 20% (w/v), 40% (w/v), 60% (w/v), 80% (w/v), and 100% (w/v).

A temperature at which the permeation step B is performed is not particularly limited. The permeation step B is preferably performed at a temperature falling within a range of 0° C. or more and not more than 40° C. A time for which the permeation step B is performed is not particularly limited. The permeation step B is performed for a time falling within a range preferably of one hour or more and not more than 14 days, and more preferably of three hours or more and not more than three days. In a case where the number of the clearing reagents B is two or more, it is preferable to set processing times of the clearing reagents B at the respective concentrations to be substantially equal. However, setting of the processing times is not limited to such setting. For example, in the case of using the clearing reagents B in which fructose is contained at the respective concentrations of 20% (w/v), 40% (w/v), 60% (w/v), 80% (w/v), and 100% (w/v), the processing times can be set at 40 hours in total by setting each of the processing times at 8 hours. A pressure at which the permeation step B is performed is not particularly limited.

In the permeation step A and the permeation step B, an order in which the "clearing reagents" and the "biological material" are stored in the container for the clearing treatment is not particularly limited. In an example in which the permeation step A and the permeation step B are continuously performed in a single container, the "clearing reagent B" which is the lowest in concentration is stored in the container first and subsequently the "biological material" is stored in the container. Next, the "clearing reagent B" which is the lowest in concentration is disposed of and the "clearing reagent B" which is the second lowest in concentration is stored in the container. Then, the "clearing reagent B" which is the second lowest in concentration is disposed of and the "clearing reagent B" which is the third lowest in concentration is stored in the container. By repeating such disposal and storage, the "clearing reagent B" which is the highest in concentration is stored in the container and disposed of. Finally, the clearing reagent A (higher in concentration than the clearing reagent B which is the highest in concentration) is stored in the container and disposed of. Further, if necessary, it is possible to provide a step of, for example, rinsing the container and/or the biological material while the clearing reagents which differ in concentration are being replaced with each other.

The container for the clearing treatment which is used in each of the above permeation steps and in which the biological material having been subjected to the clearing treatment is stored may be preserved, e.g., at room temperature or in a low-temperature environment until the container is used in the below-described observation step. (A step for preserving a sample after a clearing treatment)

(Subject Biological Material)

A biological material to be subjected to a method according to the present invention is not limited to any specific kind. The biological material is derived preferably from a plant or an animal, more preferably from an animal such as the one selected from fish, amphibians, reptiles, birds, and mammals, and particularly preferably from a mammal. The mammal is not limited to any specific kind, examples of which encompass: laboratory animals such as mice, rats, rabbits, guinea pigs, and primates except for humans; pet animals such as dogs and cats; farm animals such as cows, horses, and pigs; and humans.

Alternatively, the biological material may be an individual itself (except for a living human individual). Further alternatively, the biological material may be an organ, a tissue, or a cell taken from an individual of a multicellular organism or artificially cultured. The "clearing reagent" used in the present invention has excellent ability to make a subject transparent; therefore, even if the biological material is a tissue or an organ (e.g., the whole of or part of a brain) derived from a multicellular animal or an individual itself (e.g., an embryo) of a multicellular animal which is not a human, the biological material can be subjected to the present invention.

Since the "clearing reagent" used in the present invention causes almost neither swelling nor shrinkage of the biological material (also see Examples) and yields an extremely great effect of preventing deformation of the biological material, the "clearing reagent" is particularly suitable to make a fragile biological material transparent. Note here that examples of the fragile biological material encompass: a newborn mouse brain; a section of a tissue derived from a multicellular animal; an animal embryo at an early stage of development; and a brain of small fish such as zebra fish.

Since the "clearing reagent" used in the present invention contains, as an active component, fructose, which is a nondenaturing agent, the "clearing reagent" is less likely to cause a break in a fine structure of the biological material, so that an artifact can be less likely to occur. This allows a more accurate observation of a fine structure such as a neural circuit. Accordingly, the method of the present invention is suitably usable particularly in a case where the biological material is a tissue (such as a brain) including a neural circuit.

Further, specific examples of the biological material encompass: a biological tissue having a fluorescent chemical substance injected thereto; a biological tissue stained with a fluorescent chemical substance; a biological tissue having a fluorescent protein-expressed cell transplanted thereto; and a biological tissue taken from a genetically-modified animal in which a fluorescent protein is expressed. Examples of the fluorescent protein encompass: YFP, GFP, and tdTomato. The "clearing reagent" used in the present invention allows imaging of up to approximately 4 mm in depth for a brain tissue with use of a multiphoton microscope. In addition, the method of the present invention, which method prevents swelling of a brain tissue, allows imaging of a substantially greater depth than a conventional method which allows imaging of a depth which is substantially as great as the depth that can be imaged by the method of the present invention (but causes swelling of a brain tissue). This allows imaging of fluorescence localized at a greater depth.

Further, the biological material, which may be either of (i) a material fixed with, for example, paraformaldehyde for a microscopic observation and (ii) a non-fixed material, is preferably a fixed material.

A thickness of the biological material is not particularly limited. For example, the biological material can have a thickness of 0.05 mm to 30 mm, and preferably has a thickness of 0.2 mm to 10 mm. Since the "clearing reagent" used in the present invention allows imaging of a greater depth, the method according to the present invention may be applied to the biological material having a thickness of 0.1 mm or more.

(Making Biological Material Transparent)

Use of the method according to the present invention for making a biological material transparent allows the biological material to be made transparent. Note here that "making a biological material transparent" means that a biological material becomes more transparent than the biological material before the method according to the present invention is applied thereto, and preferably means that a biological material becomes more capable of transmitting light having a wavelength of 400 µm to 1300 µm than the biological material before the method according to the present invention is applied thereto.

(Step of Observing Biological Material Made Transparent)

The biological material made transparent is subsequently subjected to, for example, a step of observing the biological material (observation step) by an optical microscope. On the biological material to be subjected to the observation step, a visualizing treatment step (e.g., staining or marking) may be performed (i) before the method according to the present invention for making a biological material transparent (a "clearing treatment step") or (ii) after the clearing treatment step but before the observation step, if necessary.

For example, in a case where the visualizing treatment step involves use of a fluorescent protein, a fluorescent protein gene is transferred into a living biological material before the clearing treatment step so that the fluorescent protein will be expressed therein.

In a case where the visualizing treatment step is (i) injection of a fluorescent chemical substance (which is not a fluorescent protein) into a biological material or (ii) staining of a biological material with a fluorescent chemical substance, the visualizing treatment step is preferably performed before the clearing treatment step. However, such the visualizing treatment step may be performed after the clearing treatment step. Alternatively, the visualizing treatment step may be staining of a biological material with a chemical substance which is not a fluorescent chemical substance.

The observation step can be performed with use of any type of optical microscope. For example, the observation step can be performed by employing a three-dimensional super-resolution microscopy technique. Preferably, the observation step is performed by employing a confocal laser microscope, a digital scanned light-sheet microscope, or a multi-photon excitation type (generally, two-photon excitation type) optical microscopy technique.

A temperature at which the observation step is performed is not particularly limited. From the viewpoint of prevention of precipitation of fructose, the observation step may be preferably performed at a temperature equal to a temperature at which the clearing treatment step is performed.

(Other Applications)

A clearing treatment using a "clearing reagent" of the present invention is reversible. As such, a biological material having been subjected to the clearing treatment can be brought back to a state that it had before the clearing treatment, e.g., by immersing the biological material in a balanced salt solution so as to remove therefrom the components of the clearing reagent. Examples of the balanced salt solution encompass: balanced salt solutions (e.g., PBS and HBSS) which are buffered by phosphate; a balanced salt solution (TBS) which is buffered by tris hydrochloride; and basal media for cell culturing, such as MEM, DMEM, and Ham's F-12.

The use in the present invention of the "clearing reagent", which contains, as an active component, fructose, which is a nondenaturing agent, does not cause denaturation of a protein, etc. in the biological material, before and after the clearing treatment, or in a case where, after the clearing treatment, the biological material is brought back to a state that it had before the clearing treatment. Accordingly, antigenicity of the protein, etc. in the biological material is preserved as unchanged. As such, for example, after a biological material is subjected to a clearing treatment and an optical microscopic observation, the biological material can be brought back to a state that it had before the clearing treatment, so as to undergo, e.g., a detailed assay by means of generally-known tissue staining or immunostaining.

[Clearing Reagent]

The "clearing reagent" according to the present invention, which is a clearing reagent for making a biological material transparent, is a solution containing fructose. Examples of the "clearing reagent" according to the present invention encompass: the "clearing reagent A" (described earlier) and the "clearing reagents B" (described earlier). These "clearing reagents" are as described above.

The "clearing reagents" according to the present invention are suitably used in the "method for making a biological material transparent" (described earlier).

[Kit for Clearing Treatment for Making Biological Material Transparent]

A "kit for a clearing treatment for making a biological material transparent" according to the present invention includes a solution containing fructose (corresponding to the "clearing reagent A"). The "kit for a clearing treatment for making a biological material transparent" according to the present invention preferably further includes one or more solutions each containing fructose at a lower concentration than the solution (corresponding to the "clearing reagents B"). Note that the concentrations of fructose contained in the solutions are as described above in the descriptions of the "clearing reagent A" and the "clearing reagents B".

The "kit for a clearing treatment for making a biological material transparent" according to the present invention preferably further includes an "instruction manual for the kit". In the "instruction manual for the kit", recorded is, for example, how to perform the method for making a biological material transparent using the clearing reagent A and preferably further using the clearing reagents B, as described earlier in (Outline) of [Method for Making Biological Material Transparent].

Further, the "kit for a clearing treatment for making a biological material transparent" according to the present invention may include at least one selected from: a "container for a clearing treatment" used in the clearing treatment step; a "biological material holding tool (e.g., tweezers)"; and a "balanced salt solution" for bringing a biological material having been subjected to a clearing treatment back to a state that it had before the clearing treatment.

The "kit for a clearing treatment for making a biological material transparent" according to the present invention is suitably used in the "method for making a biological material transparent".

[Conclusion]

As described earlier, a method according to the present invention for making a biological material transparent, includes the step of: (a) making the biological material transparent by causing a solution containing fructose to permeate into the biological material.

The method according to the present invention is preferably arranged such that the solution contains the fructose at a concentration falling within a range of 50% (w/v) or more and not more than 200% (w/v).

The method according to the present invention is more preferably arranged such that the solution contains the fructose at a saturated concentration.

The method according to the present invention is preferably arranged such that the solution is an aqueous solution.

The method according to the present invention is preferably arranged to further include the step of: (b) prior to the step (a), causing one or more solutions each containing fructose at a lower concentration than the solution to permeate into the biological material in an ascending order of concentration.

The method according to the present invention is more preferably arranged such that the one or more solutions are each an aqueous solution.

The method according to the present invention is preferably arranged such that the biological material is (i) a tissue or an organ derived from a multicellular animal or (ii) an individual of a multicellular animal which is not a human.

The method according to the present invention is preferably arranged such that the biological material contains a cell in which a fluorescent protein is expressed.

A clearing reagent according to the present invention for making a biological material transparent, is a solution containing fructose.

A kit according to the present invention for a clearing treatment for making a biological material transparent, includes a solution containing fructose.

The following description more specifically discusses the present invention with reference to Examples and Comparative Examples. It goes without saying that the present invention is not limited to the following Examples and the present invention can have various aspects for details. The present invention is not limited to the description of the embodiments above, but may be altered by a skilled person within the scope of the claims. An embodiment based on a proper combination of technical means disclosed in different embodiments is encompassed in the technical scope of the present invention. Further, all the literatures disclosed herein and all the disclosures in the basic application of the present application (Japanese Patent Application, Tokugan, No. 2012-141488) are quoted as a part of the specification of the present invention.

EXAMPLES

Example 1

Making Mouse Brain and Fetus Transparent with Use of Fructose (Method)
A wild-type (C57BL/6N) mouse of seven days after birth was fixed by perfusion with 4% paraformaldehyde, and a part of a brain (forebrain) thereof was taken out. Further, a wild-type mouse fetus at embryonic day 12 was taken out from the mother thereof. Then, these samples were fixed with 4% paraformaldehyde at 4° C. for 12 hours. The samples thus fixed were immersed at 25° C. in a 20% (w/v) fructose aqueous solution for eight hours, in a 40% (w/v) fructose aqueous solution for eight hours, in a 60% (w/v) fructose aqueous solution for eight hours, in a 80% (w/v) fructose aqueous solution for eight hours, in a 100% (w/v) fructose aqueous solution for eight hours, and in a 110% (w/v) fructose aqueous solution for 24 hours, in this order. Note that these fructose aqueous solutions were each an aqueous solution prepared by dissolving only fructose in pure water.

Figure 1:
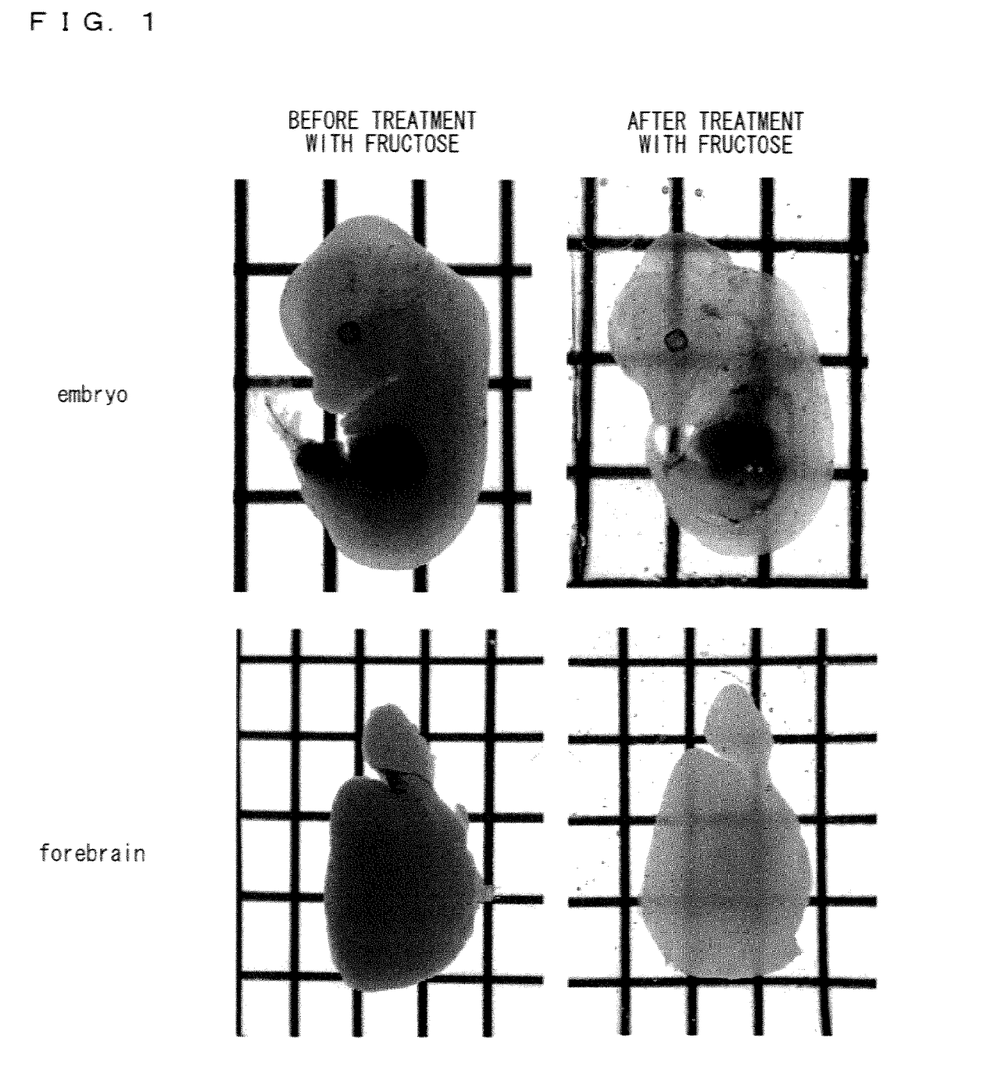
FIG. 1 illustrates a mouse fetus and a mouse brain before and after a treatment with fructose performed thereon according to a first example of the present invention.

(Result)
FIG. 1 illustrates a fetus and a brain (forebrain) before and after a treatment with fructose performed thereon. As illustrated in FIG. 1, it is revealed that the treatment with fructose made the fetus and the brain transparent.

Example 2

Observation 1 with Use of Multiphoton Microscope (Method)
A Thy1-YFP (line G) transgenic mouse of 18 days after birth (reference: Feng et al., Neuron 28, 41-51(2000)) was fixed by perfusion with 4% paraformaldehyde, and a brain thereof was taken out. Then, the brain taken out was fixed with 4% paraformaldehyde at 4° C. for 12 hours. The brain thus fixed was embedded in 2% agarose and appropriately trimmed. The brain thus trimmed was immersed at 25° C. in a 20% (w/v) fructose aqueous solution for eight hours, in a 40% (w/v) fructose aqueous solution for eight hours, in a 60% (w/v) fructose aqueous solution for eight hours, in a 80% (w/v) fructose aqueous solution for eight hours, in a 100% (w/v) fructose aqueous solution for eight hours, and in a 110% (w/v) fructose aqueous solution for 24 hours, in this order. Note that these fructose aqueous solutions were each an aqueous solution prepared by dissolving only fructose in pure water.

A cover glass was placed on an agarose block subjected to a treatment with fructose, and an olfactory bulb was observed with use of an upright two-photon microscope (product name: FV1000MPE, manufactured by Olympus Corporation, and using XLPLN25XWMP as an objective lens). Note that the objective lens used for the observation had a working distance of 2 mm. Note also that the observation was performed at 25° C.

Figure 2:
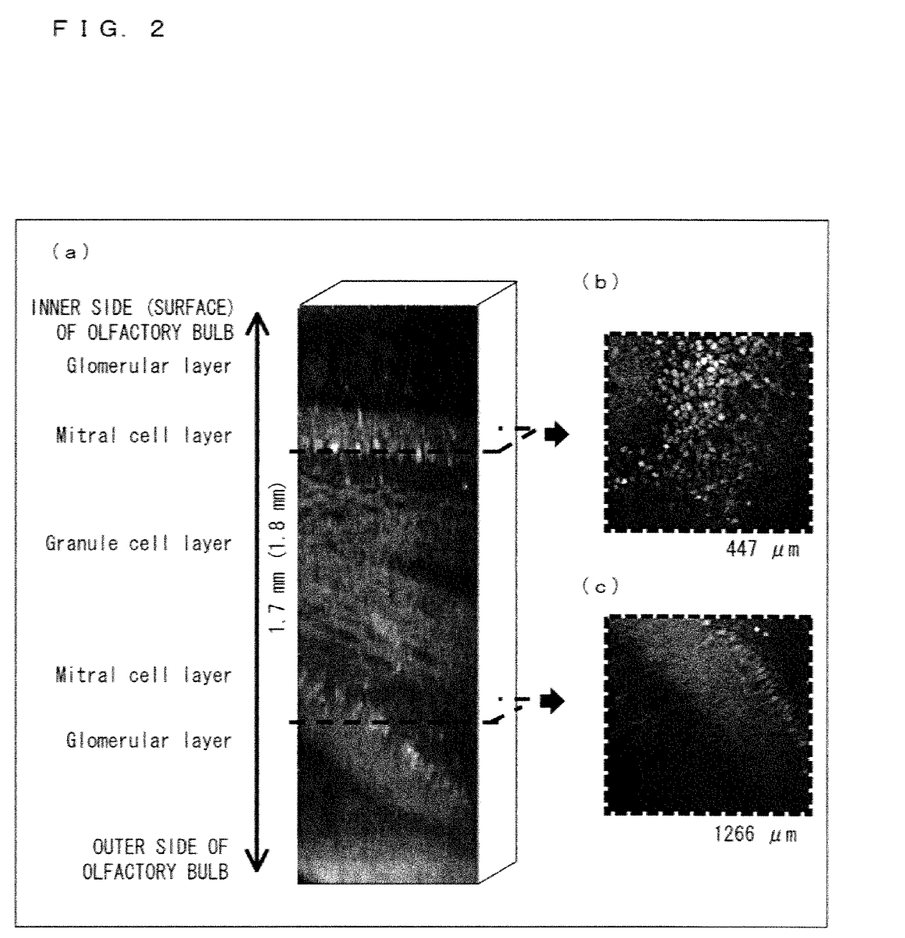
FIG. 2 illustrates a multiphoton microscope image of a mouse olfactory bulb according to a second example of the present invention.

(Result)
FIG. 2 shows a result of the observation. FIG. 2 illustrates a microscope image obtained by imaging an olfactory bulb from its inner side to its outer side. (a) of FIG. 2 illustrates an image of an optical cross section obtained by cutting in an axial direction, (b) of FIG. 2 illustrates an image of a cross section at a depth of 447 µm, and (c) of FIG. 2 illustrates an image of a cross section at a depth of 1266 µm. The imaging from the inner side of the olfactory bulb as described above made it possible to obtain a clear image of up to the outer side (approximately 1.7 mm in depth (actually, approximately 1.8 mm in depth after calibration for the refractive index).

It has been necessary to prepare a section of an olfactory bulb so as to obtain an entire three-dimensional image of the olfactory bulb. However, use of the method of the present invention makes it possible to obtain a clear image of such a deep part as described above, and thus it is possible to obtain the olfactory bulb in the form of the entire three-dimensional image by stitching images.

Example 3

Expansion and Shrinkage of Samples (Method)
A Thy1-YFP (line G) transgenic mouse of eight weeks after birth was fixed by perfusion with 4% paraformaldehyde, and a brain thereof was taken out. Then, the brain taken out was fixed with 4% paraformaldehyde at 4° C. for 12 hours. The brain thus fixed was immersed at 25° C. in a 20% (w/v) fructose aqueous solution for 12 hours, in a 40% (w/v) fructose aqueous solution for 12 hours, in a 60% (w/v) fructose aqueous solution for 12 hours, in a 80% (w/v) fructose aqueous solution for 12 hours, and in a 110% (w/v) fructose aqueous solution for 19 days, in this order. Thereafter, the brain thus immersed was returned to and immersed in 1×PBS for three days. Note that these fructose aqueous solutions were each an aqueous solution prepared by dissolving only fructose in pure water.

A brain taken out as a comparative example as in the case of the brain of Example 3 was immersed at 25° C. for 21 days in a reagent S (an aqueous solution prepared by dissolving in pure water (i) urea at a concentration of 4M, (ii) TritonX-100 (Registered Trademark) at a concentration of 0.1% (w/v), and (iii) glycerol at a concentration of 10% (w/v)). Thereafter, the brain thus immersed was returned to and immersed in 1×PBS for three days.

Expansion and shrinkage of the brain treated with fructose and in the brain treated with the reagent S was examined before the treatment (at the zeroth day); at 0.5 day, one day, 1.5 day, two days, and 21 days after the start of the clearing treatment; and at one day, two days, and three days after the return to PBS.

Figure 3:
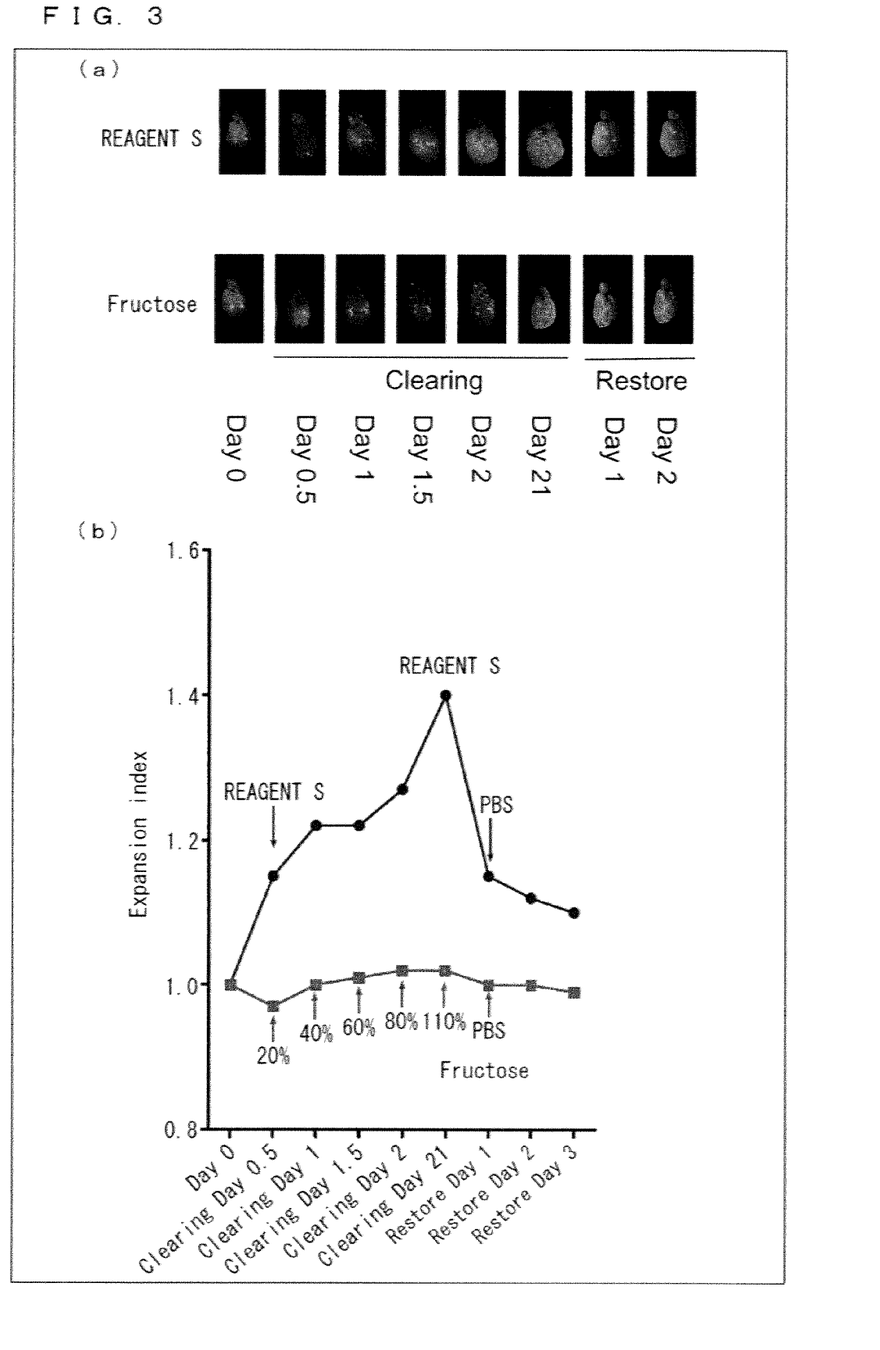
FIG. 3 shows expansion and shrinkage of a sample according to a third example of the present invention, the sample having been made transparent.

(Result)
FIG. 3 shows a result of expansion and shrinkage of samples. (a) of FIG. 3 illustrates an entire image of a brain at each day. (b) of FIG. 3 is a graph showing an expansion index (one-dimensional) at each day assuming that the size of the brain at the zeroth day is one. As illustrated in (a) and (b) of FIG. 3, use of the reagent S caused swelling over time in the brain and caused shrinkage of the brain which was returned to PBS. In contrast, use of fructose with an increase in concentration caused almost neither swelling nor shrinkage of the brain. Further, the brain which was returned to PBS was substantially unchanged.

As described above, the use of fructose allowed the samples to be transparent with their volume substantially unchanged.

Example 4

Change in Cell Morphology and Antigenicity (Method)

A Thy1-YFP (line G) transgenic mouse of eight weeks after birth was fixed by perfusion with 4% paraformaldehyde, and a brain thereof was taken out. Then, the brain taken out was fixed with 4% paraformaldehyde at 4° C. for 12 hours. The brain thus fixed was immersed at 25° C. in a 20% (w/v) fructose aqueous solution for eight hours, in a 40% (w/v) fructose aqueous solution for eight hours, in a 60% (w/v) fructose aqueous solution for eight hours, in a 80% (w/v) fructose aqueous solution for eight hours, in a 100% (w/v) fructose aqueous solution for eight hours, and in a 110% (w/v) fructose aqueous solution for 24 hours, in this order. Thereafter, the brain thus immersed was returned to 1×PBS, treated with 30% (w/v) sucrose, and embedded in a frozen tissue embedding agent (O.C.T. compound). Subsequently, the brain was frozen for one hour and then a brain section having a thickness of 20 μm was prepared. Gephyrin, which is an inhibitory postsynaptic marker protein, was stained. Specifically, the brain section was reacted with an anti-Gephyrin rabbit antibody (manufactured by Abcam plc.) (200-fold diluted) for one hour and then rinsed with PBS three times. Subsequently, the brain section was reacted with an Alexa Fluor647-labeled anti-rabbit antibody (200-fold diluted) for 40 minutes and then rinsed with PBS three times. The brain section was nuclear-stained with DAPI. Note that the fructose aqueous solutions were each an aqueous solution prepared by dissolving only fructose in pure water.

A brain taken out as a comparative example as in the case of the brain of Example 4 was immersed for 21 days in a reagent S (an aqueous solution prepared by dissolving in pure water (i) urea at a concentration of 4M, (ii) TritonX-100 (Registered Trademark) at a concentration of 0.1% (w/v), and (iii) glycerol at a concentration of 10% (w/v)) (in the case of the reagent S, it takes a longer time for the brain to be made transparent and thus a processing time is made longer, as compared with the case of the fructose aqueous solutions). Thereafter, the brain thus immersed was returned to 1×PBS and stained as in the case of the brain of Example 4.

Fluorescence of the brain section treated with fructose and of the brain section treated with the reagent S was observed by use of an inverted fluorescence microscope (model number: DMI6000B, manufactured by Leica Microsystems). Due to significant decay of fluorescence from YFP of a sample which is the comparative example and has been treated with the reagent S, an image of YFP was obtained by causing the sample to be exposed to light longer than the other samples.

(Result)

Figure 4:
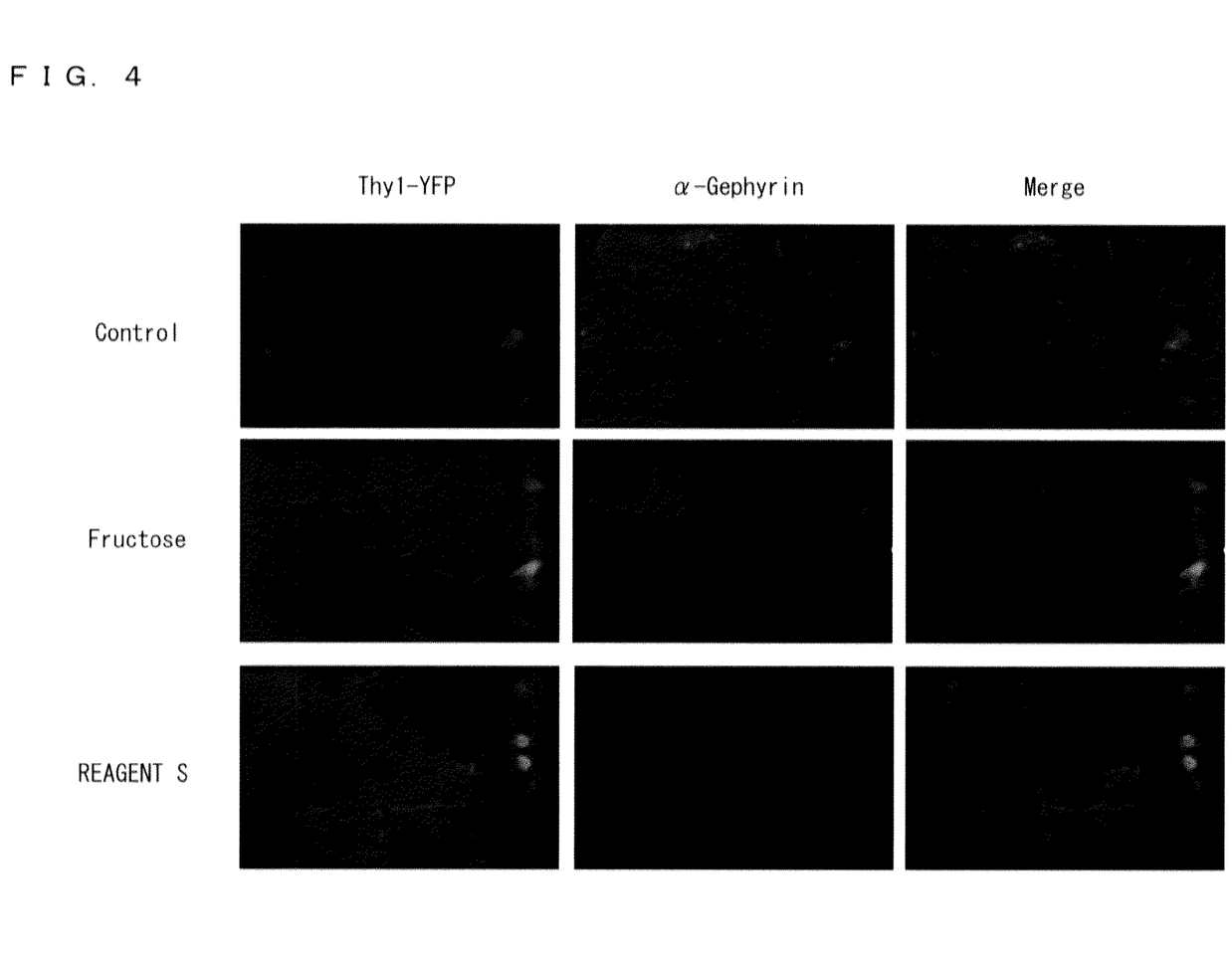
FIG. 4 shows a change in cell morphology and antigenicity according to a fourth example of the present invention.

FIG. 4 illustrates images obtained by use of a microscope. For reference, FIG. 4 also illustrates images of a brain section which is not subjected to a clearing treatment (Control). As illustrated in FIG. 4, fructose more successfully prevented a change in cell morphology and antigenicity than the reagent S.

Example 5

Observation 2 with Use of Multiphoton Microscope (Method)

A Thy1-YFP (line G) transgenic mouse of three weeks after birth was fixed by perfusion with 4% paraformaldehyde, and a brain thereof was taken out. Then, the brain taken out was fixed with 4% paraformaldehyde at 4° C. for 12 hours. The brain thus fixed was embedded in 2% (w/v) agarose and appropriately trimmed. The brain thus trimmed was immersed at 25° C. in a 20% (w/v) fructose aqueous solution for eight hours, in a 40% (w/v) fructose aqueous solution for eight hours, in a 60% (w/v) fructose aqueous solution for eight hours, in a 80% (w/v) fructose aqueous solution for eight hours, in a 100% (w/v) fructose aqueous solution for eight hours, and in a 110% (w/v) fructose aqueous solution for 24 hours, in this order. Note that these fructose aqueous solutions were each an aqueous solution prepared by dissolving only fructose in pure water.

A cover glass was placed on an agarose block subjected to a treatment with fructose, and a cerebral cortex was observed with use of an upright multiphoton microscope (product name: FV1000MPE, manufactured by Olympus Corporation, and using XLPLN25XSVMP as an objective lens). Note that the objective lens used for the observation had a working distance of 4 mm. Note also that the observation was performed at 25° C.

(Result)

Figure 5:
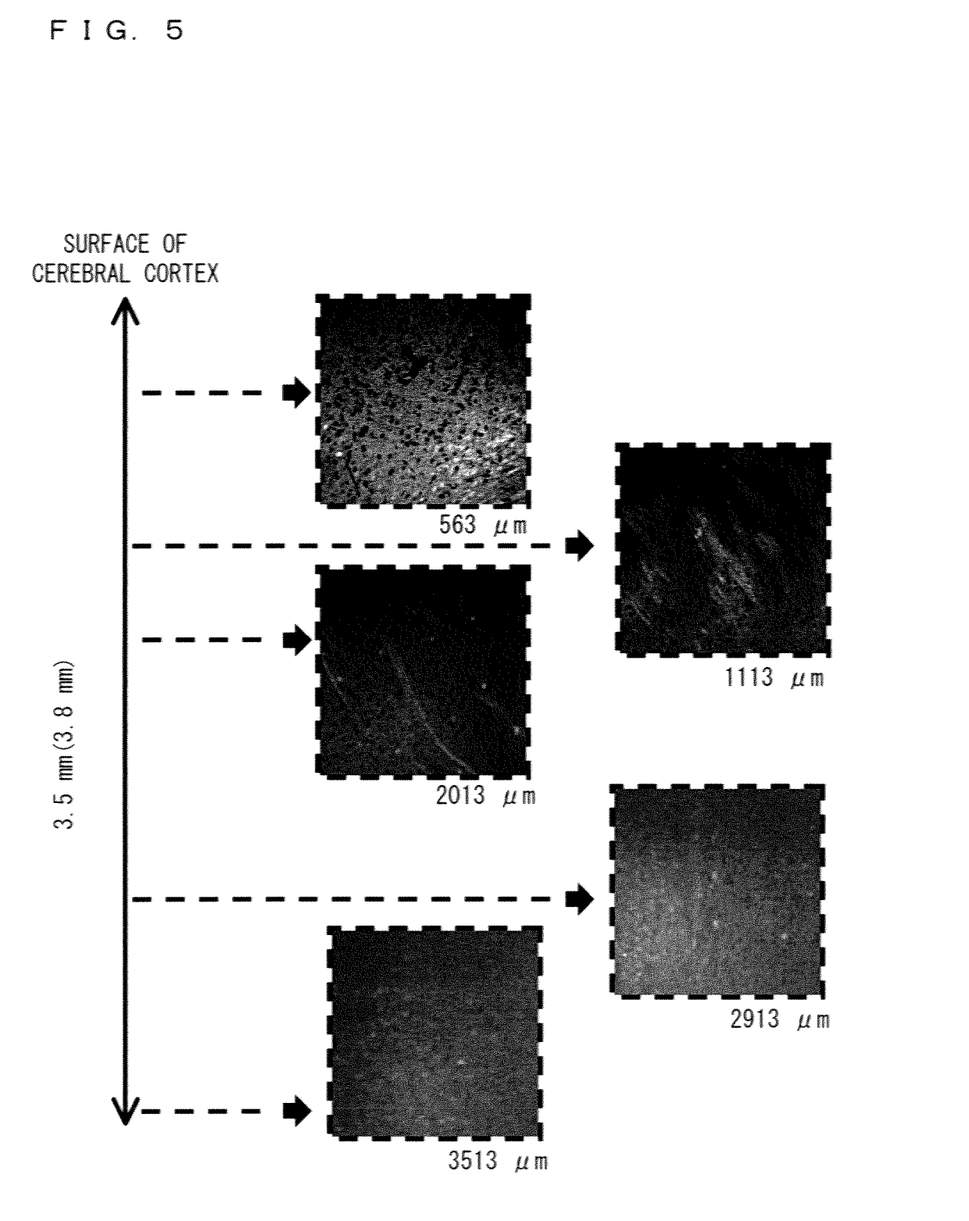
FIG. 5 shows a multiphoton microscope image of a mouse cerebral cortex according to a fifth example of the present invention.

FIG. 5 shows a result of the observation. FIG. 5 illustrates microscope images obtained by imaging a cerebral cortex from its lateral surface. The microscope images are images of cross sections at respective depths of 563 μm, 1113 μm, 2013 μm, 2913 μm, and 3513 μm. The imaging as described above made it possible to obtain a clear image of up to 3.5 mm in depth (actually, 3.8 mm in depth after calibration for the refractive index) (restricted substantially by a working distance of the objective lens). There is a possibility that future development of an objective lens having a longer working distance will allow observation of a deeper part.

INDUSTRIAL APPLICABILITY (i) A method according to the present invention for making a biological material transparent, (ii) a clearing reagent according to the present invention for making a biological material transparent, and (iii) a kit according to the present invention for a clearing treatment for making a biological material transparent can each be used to make a biological material transparent without denaturing protein.

The invention claimed is:

1. A combination of clearing reagents for making a biological material transparent, comprising:
   a first clearing reagent which is a fructose solution containing 80% of a saturated concentration of fructose to 100% of a saturated concentration of fructose; and
   additional clearing reagents which are fructose solutions containing fructose at concentrations lower than that of the fructose contained in the first solution,
   the first clearing reagent and the additional clearing reagents are used in respective different steps of a method for making a biological material transparent, the method comprising the steps of:
   (a) treating the biological material with each of said additional clearing reagent solutions in ascending order of fructose concentration and causing the clearing reagents to permeate into the biological material; and
   (b) treating the biological material obtained after treatment according to step (a) with said first clearing reagent and causing the first clearing reagent to permeate into the biological material, thereby making the biological material transparent.

2. The combination as set forth in claim 1, wherein the first solution contains the fructose at a concentration of 50% (w/v) to 200% (w/v).

3. The combination as set forth in claim 1, wherein the first solution is an aqueous solution.

4. The combination as set forth in claim 1, wherein the biological material is (i) a whole of a multicellular animal which is not a human or (ii) a brain tissue.

5. The combination as set forth in claim 1, wherein the biological material contains a cell in which a fluorescent protein is expressed.

\* \* \* \* \*